United States Patent [19]
Berg et al.

[11] Patent Number: 4,994,151
[45] Date of Patent: * Feb. 19, 1991

[54] SEPARATION OF 4-METHYL-2-PENTANONE FROM FORMIC ACID BY EXTRACTIVE DISTILLATION WITH DIMETHYLAMIDES

[75] Inventors: Lloyd Berg, 1314 S. 3rd Ave., Bozeman, Mont. 59715; George Bentu, Bozeman, Mont.

[73] Assignee: Lloyd Berg, Bozeman, Mont.

[*] Notice: The portion of the term of this patent subsequent to Jun. 20, 2006 has been disclaimed.

[21] Appl. No.: 380,018

[22] Filed: Jul. 14, 1989

[51] Int. Cl.$^5$ .................... B01D 3/40; C07C 45/83; C07C 53/02
[52] U.S. Cl. .................... 203/51; 203/56; 203/60; 203/61; 203/62; 203/63; 203/64; 203/65; 562/609; 568/410
[58] Field of Search .................... 203/51, 60, 61, 62, 203/63, 56, 64, 65; 568/410; 562/609

[56] References Cited

U.S. PATENT DOCUMENTS

| | | | |
|---|---|---|---|
| 3,013,954 | 12/1961 | Pacoud et al. | 203/62 |
| 4,551,208 | 11/1985 | Bott et al. | 203/60 |
| 4,793,901 | 12/1988 | Berg et al. | 203/60 |
| 4,840,707 | 6/1989 | Berg et al. | 203/60 |

Primary Examiner—Wilbur Bascomb

[57] ABSTRACT

4-Methyl-2-pentanone cannot be easily separated from formic acid by distillation because of the closeness of their boiling points. 4-Methyl-2-pentanone can be readily removed from formic acid by extractive distillation using dimethylamides. Typical effective agents are dimethylformamide; dimethylacetamide and acetyl salicyclic acid; dimethylacetamide, heptanoic acid and methyl benzoate.

2 Claims, No Drawings

SEPARATION OF 4-METHYL-2-PENTANONE FROM FORMIC ACID BY EXTRACTIVE DISTILLATION WITH DIMETHYLAMIDES

FIELD OF THE INVENTION

This invention relates to a method for separating 4-methyl-2-pentanone from formic acid using certain dimethylamides as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centrigrade degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

4-Methyl-2-pentanone, B. P. = 117° C. and formic acid, B. P. = 101° C. possess an average relative volatility of about 1.3 and boil so close together that they are difficult to separate by conventional rectification. Extractive distillation would be an attractive method of effecting the separation of 4-methyl-2-pentanone from formic acid if agents can be found that (1) will enhance the relative volatility of 4-methyl-2-pentanone to formic acid and (2) are easy to recover from the formic acid, that is, form no azeotrope with formic acid and boil sufficiently above formic acid to make separation by rectification possible with only a few theoretical plates.

Extractive distillation typically requires the addition of an equal amount to twice as much extractive agent as the 4-methyl-2-pentanone-formic acid on each plate of the rectification column. The extractive agent should be heated to about the same temperature as the plate on to which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

Berg, U.S. Pat. No. 4,692,219 separated formic acid from acetic acid by extractive distillation. Extractive distillation was used by Berg, U.S. Pat. No. 4,735,690 to remove water and impurities from formic acid and Berg, U.S. Pat. No. 4,793,901 to break the 2-pentanone-formic acid azeotrope.

OBJECTIVE OF THE INVENTION

The object of this invention is to provide a process or method of extractive distillation that will enhance the relative volatility of 4-methyl-2-pentanone from formic acid in their separation in a rectification column. It is a further object of this invention to identify suitable extractive distillation agents that will separate the 4-methyl-2-pentanone-formic acid mixture and make possible the production of pure 4-methyl-2-pentanone and formic acid by rectification. It is a further object of this invention to identify certain amides which in addition to the above constraints, are stable, can be separated from formic acid by rectification with relatively few theoretical plates and can be recycled to the extractive distillation column and reused with little or no decomposition.

SUMMARY OF THE INVENTION

The objects of the invention are provided by a process for separating 4-methyl-2-pentanone from formic acid which entails the use of dimethyl-formamide or dimethylacetamide, either alone or admixed with certain oxygenated organic compounds as the agents in extractive distillation.

TABLE 1

Effective Extractive Distillation Agents Containing DMFA

| Compounds | Ratios | | Relative Volatilities | |
| --- | --- | --- | --- | --- |
| Dimethylformamide (DMFA) | 1 | 6/5 | 2.0 | 1.9 |
| DMFA, Hexanoic acid | (½)² | (3/5)² | 1.7 | 1.3 |
| DMFA, Heptanoic acid | (½)² | (3/5)² | 1.1 | 1.3 |
| DMFA, Itaconic acid | (½)² | (3/5)² | 1.2 | 1.1 |
| DMFA, Neodecanoic acid | (½)² | (3/5)² | 1.2 | 1.1 |
| DMFA, Octanoic acid | (½)² | (3/5)² | 1.4 | 1.2 |
| DMFA, Pelargonic acid | (½)² | (3/5)² | 1.2 | 1.1 |
| DMFA, Hexanoic acid, Methyl benzoate | (⅓)³ | (2/5)³ | 1.6 | 1.4 |
| DMFA, Heptanoic acid, Ethyl benzoate | (⅓)³ | (2/5)³ | 1.3 | 1.3 |
| DMFA, Itaconic acid, 2-Octanone | (⅓)³ | (2/5)³ | 1.2 | 1.4 |
| DMFA, Neodecanoic acid, Benzyl acetate | (⅓)³ | (2/5)³ | 1.1 | 1.4 |

TABLE 1-continued

Effective Extractive Distillation Agents Containing DMFA

| Compounds | Ratios | | Relative Volatilities | |
|---|---|---|---|---|
| DMFA, Octanoic acid, Butyl benzoate | (⅓)[3] | (2/5)[3] | 1.3 | 1.3 |
| DMFA, Pelargonic acid, Benzyl acetate | (⅓)[3] | (2/5)[3] | 1.1 | 1.5 |

TABLE 2

Effective Extractive Distillation Agents Containing DMAA

| Compounds | Ratios | | Relative Volatilities | |
|---|---|---|---|---|
| Dimethylacetamide (DMAA) | 1 | 6/5 | 1.1 | 1.2 |
| DMAA, Adipic acid | (½)[2] | (3/5)[2] | 2.5 | 2.9 |
| DMAA, Acetyl salicylic acid | (½)[2] | (3/5)[2] | 1.8 | 2.1 |
| DMAA, Azelaic acid | (½)[2] | (3/5)[2] | 3.0 | 2.1 |
| DMAA, Benzoic acid | (½)[2] | (3/5)[2] | 3.0 | 2.9 |
| DMAA, o-tert. Butyl benzoic acid | (½)[2] | (3/5)[2] | 2.0 | 1.9 |
| DMAA, Cinnamic acid | (½)[2] | (3/5)[2] | 2.3 | 1.3 |
| DMAA, Decanoic acid | (½)[2] | (3/5)[2] | 1.5 | 1.5 |
| DMAA, Dodecanedioic acid | (½)[2] | (3/5)[2] | 1.6 | 2.1 |
| DMAA, Glutaric acid | (½)[2] | (3/5)[2] | 2.0 | 2.1 |
| DMAA, Heptanoic acid | (½)[2] | (3/5)[2] | 3.3 | 3.1 |
| DMAA, Hexanoic acid | (½)[2] | (3/5)[2] | 2.1 | 2.1 |
| DMAA, 4-Hydroxybenzoic acid | (½)[2] | (3/5)[2] | 1.5 | 1.6 |
| DMAA, Itaconic acid | (½)[2] | (3/5)[2] | 2.2 | 2.4 |
| DMAA, Malic acid | (½)[2] | (3/5)[2] | 2.4 | 2.5 |
| DMAA, Neodecanoic acid | (½)[2] | (3/5)[2] | 1.6 | 1.8 |
| DMAA, Neopentanoic acid | (½)[2] | (3/5)[2] | 1.5 | 1.6 |
| DMAA, m-Nitrobenzoic acid | (½)[2] | (3/5)[2] | 1.6 | 2.0 |
| DMAA, Octanoic acid | (½)[2] | (3/5)[2] | 1.6 | 2.1 |
| DMAA, Pelargonic acid | (½)[2] | (3/5)[2] | 1.7 | 2.1 |
| DMAA, Salicylic acid | (½)[2] | (3/5)[2] | 1.6 | 1.3 |
| DMAA, Sebacic acid | (½)[2] | (3/5)[2] | 1.3 | 1.6 |
| DMAA, o-Toluic acid | (½)[2] | (3/5)[2] | 1.9 | 1.9 |
| DMAA, m-Toluic acid | (½)[2] | (3/5)[2] | 2.1 | 1.9 |
| DMAA, p-Toluic acid | (½)[2] | (3/5)[2] | 1.7 | 1.5 |
| DMAA, 3,4,5-Trimethoxy benzoic acid | (½)[2] | (3/5)[2] | 1.9 | 1.5 |
| DMAA, Undecanoic acid | (½)[2] | (3/5)[2] | 1.6 | 2.2 |
| DMAA, Adipic acid, Diisobutyl ketone | (⅓)[3] | (2/5)[3] | 2.4 | 1.9 |
| DMAA, Acetyl salicylic acid, Acetophenone | (⅓)[3] | (2/5)[3] | 1.9 | 1.8 |
| DMAA, Azelaic acid, Adiponitrile | (⅓)[3] | (2/5)[3] | 2.6 | 2.4 |
| DMAA, Benzoic acid, Anisole | (⅓)[3] | (2/5)[3] | 1.3 | 1.6 |
| DMAA, o-tert. Butyl benzoic acid, Methyl salicylate | (⅓)[3] | (2/5)[3] | 2.0 | 1.7 |
| DMAA, Cinnamic acid, Butyl ether | (⅓)[3] | (2/5)[3] | 2.5 | 2.8 |
| DMAA, Decanoic acid, Cyclo hexanone | (⅓)[3] | (2/5)[3] | 1.7 | 1.8 |
| DMAA, Dodecanedioic acid, Diisobutyl ketone | (⅓)[3] | (2/5)[3] | 1.4 | 1.4 |
| DMAA, Glutaric acid, Methyl isoamyl ketone | (⅓)[3] | (2/5)[3] | 1.9 | 2.7 |
| DMAA, Heptanoic acid, Ethyl benzoate | (⅓)[3] | (2/5)[3] | 2.6 | 2.1 |
| DMAA, Hexanoic acid, Methyl benzoate | (⅓)[3] | (2/5)[3] | 1.5 | 1.2 |
| DMAA, 4-Hydroxybenzoic acid, Ethylene glycol diacetate | (⅓)[3] | (2/5)[3] | 1.6 | 1.3 |
| DMAA, Itaconic acid, 2-Octanone | (⅓)[3] | (2/5)[3] | 1.7 | 2.9 |
| DMAA, Malic acid, Diethylene glycol dibenzoate | (⅓)[3] | (2/5)[3] | 1.5 | 1.2 |
| DMAA, Neodecanoic acid, Isophorone | (⅓)[3] | (2/5)[3] | 1.8 | 1.5 |
| DMAA, Neopentanoic acid, 2-Heptanone | (⅓)[3] | (2/5)[3] | 1.3 | 1.4 |
| DMAA, m-Nitrobenzoic acid, Hexyl acetate | (⅓)[3] | (2/5)[3] | 1.7 | 1.3 |
| DMAA, p-Nitrobenzoic acid, Acetophenone | (⅓)[3] | (2/5)[3] | 1.1 | 1.1 |
| DMAA, Octanoic acid, Butyl benzoate | (⅓)[3] | (2/5)[3] | 1.7 | 1.6 |
| DMAA, Pelargonic acid, Benzyl benzoate | (⅓)[3] | (2/5)[3] | 1.1 | 1.2 |
| DMAA, Salicylic acid, Ethyl salicylate | (⅓)[3] | (2/5)[3] | 1.1 | 1.1 |
| DMAA, Sebacic acid, Ethyl butyl ketone | (⅓)[3] | (2/5)[3] | 2.1 | 1.3 |
| DMAA, o-Toluic acid, Diethylene glycol dimethyl ether | (⅓)[3] | (2/5)[3] | 1.7 | 1.7 |
| DMAA, m-Toluic acid, Diethylene glycol diethyl ether | (⅓)[3] | (2/5)[3] | 1.6 | 1.6 |
| DMAA, p-Toluic acid, Dipropylene glycol dibenzoate | (⅓)[3] | (2/5)[3] | 1.7 | 1.5 |
| DMMA, 3,4,5-Trimethoxybenzoic acid, Ethyl phenyl acetate | (⅓)[3] | (2/5)[3] | 1.6 | 1.5 |
| DMMA, Undecanoic acid, 2-Hydroxy acetophenone | (⅓)[3] | (2/5)[3] | 1.1 | 1.2 |

TABLE 3

Data From Run Made In Rectification Column

| Agent | Column | Time, hrs. | Weight % Ketone | Weight % Formic acid | Relative Volatility |
|---|---|---|---|---|---|
| 33% DMAA, 33% Heptanoic acid, 33% Methyl benzoate | Overhead | ¾ | 98.7 | 1.3 | 3.5 |
| | Bottoms | | 10.3 | 89.7 | |
| 33% DMAA, 33% Heptanoic acid, | Overhead | 1.5 | 90.9 | 9.1 | 2.9 |
| | Bottoms | | 4 | 96 | |

TABLE 3-continued

| | Data From Run Made In Rectification Column | | | | |
|---|---|---|---|---|---|
| Agent | Column | Time, hrs. | Weight % Ketone | Weight % Formic acid | Relative Volatility |
| 33% Methyl benzoate | | | | | |

DETAILED DESCRIPTION OF THE INVENTION

We have discovered that dimethylformamide (DMFA) and dimethylacetamide (DMAA), either singly or admixed with other high boiling organic compounds, will effectively increase the relative volatility of 4-methyl-2-pentanone to formic acid and permit the separation of pure 4-methyl-2-pentanone from formic acid by rectification when employed as the agent in extractive distillation. Table 1 lists the mixtures containing DMFA in the proportions that we have found to be effective. Table 2 lists the mixtures containing DMAA that are effective. The data in Tables 1 and 2 were obtained in a vapor-liquid equilibrium still. In each case, the starting mixture was 35% 4-methyl-2-pentanone, 65% formic acid. The ratios are the parts by weight of extractive agent used per part of 4-methyl-2-pentanone-formic acid mixture. The relative volatilities are listed for each of the two ratios employed. The compounds which are effective when used in mixtures with DMAA are adipic acid, acetyl salicylic acid, azelaic acid, benzoic acid, o-tert, butyl benzoic acid, cinnamic acid, decanoic acid, dodecanedioic acid, glutaric acid, heptanoic acid, hexanoic acid, 4-hydroxybenzoic acid, itaconic acid, malic acid, neodecanoic acid, neopentanoic acid, m-nitrobenzoic acid, octanoic acid, pelargonic acid, salicylic acid, sebacic acid, o-toluic acid, m-toluic acid, p-toluic acid, 3,4,5-trimethyoxy benzoic acid, undecanoic acid, diisobutyl ketone, acetophenone, adiponitrile, anisole, methyl salicylate, butyl ether, cyclohexanone, methyl isoamyl ketone, ethyl benzoate, methyl benzoate, ethylene glycol diacetate, 2-octanone, diethylene glycol dibenzoate, isophorone, 2-heptanone, hexyl acetate, butyl benzoate, benzyl benzoate, ethyl salicylate, ethyl butyl ketone, diethylene glycol dimethyl ether, diethylene glycol diethyl ether, dipropylene glycol dibenzoate, ethyl phenyl acetate and 2-hydroxy-acetophenone. The compounds which are effective when used in mixtures with DMFA are hexanoic acid, heptanoic acid, itaconic acid, neodecanoic acid, octanoic acid, pelargonic acid, methyl benzoate, ethyl benzoate, 2-octanone, benzyl acetate and butyl benzoate.

The two relative volatilities shown in Tables 1 and 2 correspond to the two different ratios investigated. For example, in Table 2, one half part of DMAA plus one half part of acetyl salicylic acid with one part of the 4-methyl-2-pentanone-formic acid mixture gives a relative volatility of 1.8; 3/5 parts of DMAA plus 3/5 parts of acetyl salicylic acid give 2.1. One third parts each of DMAA, azelaic acid and adiponitrile with one part of the 4-methyl-2-pentanone-formic acid mixture gives a relative volatility of 2.6; with 2/5 parts, these three give 2.4. In every example in Tables 1 and 2, the starting material is the 4-methyl-2-pentanone-formic acid mixture which possesses a relative volatility of 1.3.

Three of the agents, DMAA plus heptanoic acid plus methyl benzoate, listed in Table 2 and whose relative volatility had been determined in the vapor-liquid equilibrium still, were then evaluated in a glass perforated plate rectification column possessing 5.3 theoretical plates and the results listed in Table 3. The data in Table 3 was obtained in the following manner. The charge was 100 grams of 4-methyl-2-pentanone and 100 grams of formic acid and after a half hour of operation in the 5.3 theoretical plate column to establish equilibrium, DMAA, heptanoic acid and methyl benzoate at 95° C. and 38 ml/min. were pumped in. The rectification was continued with sampling of the overhead and bottoms after 45 minutes. The analyses are shown in Table 3 and were: overhead 98.7% 4-methyl-2-pentaone, 1.3% formic acid and bottoms was 10.3% 4-methyl-2-pentanone, 89.7% formic acid which gives a relative volatility of 4-methyl-2-pentanone to formic acid of 3.5. After 1.5 hours of continuous operation, overhead and bottoms were again sampled and analysed. The overhead was 90.9% 4-methyl-2-pentanone, 9.1% formic acid and the bottoms was 4% 4-methyl-2-pentanone, 96% formic acid which is a relative volatility of 2.9. This indicates that the relative volatility has been enhanced and separation accomplished by extractive distillation.

THE USEFULNESS OF THE INVENTION

The usefulness or utility of this invention can be demonstrated by referring to the data presented in Tables 1, 2 & 3. All of the successful extractive distillation agents show that 4-methyl-2-pentanone and formic acid can be separated from each other by means of distillation in a rectification column and that the ease of separation as measured by relative volatility is considerable. Without these extractive distillation agents, the relative volatility would be only 1.3 and separation by rectification would be difficult. The data also show that the most attractive agents will operate at a boilup rate low enough to make this a useful and efficient method of recovering high purity 4-methyl-2-pentanone and formic acid from any mixture of these two close boiling compounds. The stability of the compounds used and the boiling point difference is such that complete recovery and recycle is obtainable by a simple distillation and the amount required for make-up is small.

WORKING EXAMPLES

Example 1

Eighteen grams of 4-methyl-2-pentanone, 33 grams of formic acid and 50 grams of DMFA were charged to a vapor-liquid equilibrium still and refluxed for 12 hours. Analysis indicated a vapor composition of 39% 4-methyl-2-pentanone, 61% formic acid and a liquid composition of 24.1% 4-methyl-2-pentanone, 75.9% formic acid which is a relative volatility of 2.0. Ten grams of DMFA were added and refluxing continued for another 11 hours. Analysis indicated a vapor composition of 46.2% 4-methyl-2-pentanone, 53.8% formic acid, a liquid composition of 31.3% 4-methyl-2-pentanone, 68.7% formic acid which is a relative volatility of 1.9.

Example 2

Fifty grams of the 4-methyl-2-pentanone-formic acid mixture, 25 grams of DMAA and 25 grams of acetyl salicylic acid were charged to the vapor-liquid equilibrium still and refluxed for 16 hours. Analysis indicated a vapor composition of 16.3% 4-methyl-2-pentanone, 83.7% formic acid and a liquid composition of 9.8% 4-methyl-2-pentanone, 90.2% formic acid which is a relative volatility of 1.8. Five grams of DMAA and five grams of acetyl salicylic acid were added and refluxing continued for another eleven hours. Analysis indicated a vapor composition of 12.9% 4-methyl-2-pentanone, 87.1% formic acid and a liquid composition of 6.5% 4-methyl-2-pentanone, 93.5% formic acid which is a relative volatility of 2.1.

Example 3

Fifty grams of the 4-methyl-2-pentanone-formic acid mixture, 17 grams of DMAA, 17 grams of azelaic acid and 17 grams of adiponitrile were charged to the vapor-liquid equilibrium still and refluxed for 12 hours. Analysis indicated a vapor composition of 25.5% 4-methyl-2-pentanone, 74.5% formic acid and a liquid composition of 11.8% 4-methyl-2-pentanone, 88.2% formic acid which is a relative volatility of 2.6. Three grams each of DMAA, azelaic acid and adiponitrile were added and refluxing continued for another nine hours. Analysis indicated a vapor composition of 22.4% 4-methyl-2-pentanone, 77.6% formic acid and a liquid composition of 10.7% 4-methyl-2-pentanone, 89.3% formic acid which is a relative volatility of 2.4.

Example 4

A glass perforated plate rectification column was calibrated with methyl cyclohexane and toluene which possesses a relative volatility of 1.46 and found to have 5.3 theoretical plates. A solution comprising 100 grams of 4-methyl-2-pentanone and 100 grams of formic acid was placed in the stillpot and heated. When refluxing began, an extractive agent comprising 33% DMAA, 33% heptanoic acid and 33% methyl benzoate was pumped into the column at a rate of 38 ml/min. The temperature of the extractive agent as it entered the column was 95° C. After establishing the feed rate of the extractive agent, the heat input to the 4-methyl-2-pentanone and formic acid in stillpot was adjusted to give a total reflux rate of 40 ml/min. After 45 minutes of operation, the overhead and bottoms samples of approximately two ml. were collected and analysed by gas chromatography. The overhead analysis was 98.7% 4-methyl-2-pentanone and 1.3% formic acid. The bottom analysis was 10.3% 4-methyl-2-pentanone and 89.7% formic acid. Using these compositions in the Fenske equation, with the number of theoretical plates in the column being 5.3, gave an average relative volatility of 3.5 for each theoretical plate. After 1.5 hours of continuous operation, the overhead analysis was 90.7% 4-methyl-2-pentanone, 9.1% formic acid, the bottoms analysis was 4% 4-methyl-2-pentanone and 96% formic acid which is a relative volatility of 2.9. These data are presented in Table 3.

We claim:

1. A method for recovering 4-methyl-2-pentanone from mixtures of 4-methyl-2-pentanone and formic acid which comprises distilling a mixture of 4-methyl-2-pentanone and formic acid in a rectification column in the presence of about one part of an extractive agent per part of 4-methyl-2-pentanone-formic acid mixture, recovering 4-methyl-2-pentanone as overhead product and obtaining the extractive agent and the formic acid from the stillpot, wherein said extractive agent comprises dimethylacetamide and at least one material selected from the group consisting of cinnamic acid m-nitrobenzoic acid, 3,4,5-trimethoxy benzoic acid, undecanoic acid, diisobutyl ketone, acetophenone, adiponitrile, anisole, methyl isoamyl ketone, ethylene glycol diacetate, diethylene glycol dibenzoate, 2-heptanone, ethyl salicylate, ethyl butyl ketone, diethylene glycol dimethyl ether, diethylene glycol diethyl ether, dipropylene glycol dibenzoate ethyl phenyl acetate and 2-hydroxyacetophenone.

2. A method for recovering 4-methyl-2-pentanone from mixtures of 4-methyl-2-pentanone and formic acid which comprises distilling a mixture of 4-methyl-2-pentanone and formic acid in a rectification column in the presence of about one part of an extractive agent per part of the 4-methyl-2-pentanone-formic acid mixture, recovering 4-methyl-2-pentanone as overhead product and obtaining the extractive agent and the formic acid from the stillpot, wherein said extractive agent comprises dimethylformamide and at least one material selected from the group consisting of hexanoic acid, itaconic acid, 2-octanone and benzyl acetate.

* * * * *